US00PP09694P

United States Patent [19]

Henny

[11] Patent Number: Plant 9,694

[45] Date of Patent: Nov. 12, 1996

[54] DIEFFENBACHIA NAMED '61101'

[75] Inventor: Richard J. Henny, Tavares, Fla.

[73] Assignee: Florida Foundation Seed Producers, Inc., Greenwood, Fla.

[21] Appl. No.: 341,679

[22] Filed: Nov. 17, 1994

[51] Int. Cl.[6] ..... A01H 5/00

[52] U.S. Cl. ..... Plt./88.2

[58] Field of Search ..... Plt./88.2

*Primary Examiner*—James R. Feyrer

*Attorney, Agent, or Firm*—Frank B. Robb; John H. Vynalek

[57] ABSTRACT

There is disclosed a representative plant of Dieffenbachia designated 61101, which is one displaying a variety of variegated areas on each leaf, none uniform, which are enclosed by a green border and thus become distinctive in and of themselves, the variegations being repeated in all the leaves and without uniformity.

1 Drawing Sheet

BACKGROUND OF THE DISCLOSURE

This invention relates to Dieffenbachia Plants, and more particularly to a cultivar thereof which is one of a series from a long and detailed program for developing such plants and as stated is a product of the planned breeding program which has a long history and detailed information thereof available.

This program for development of Dieffenbachia, has been carried on in the vicinity of Apopka, Fla., and the particular seedling of this invention is a result of many crosses which is disclosed in an outline to be subsequently set forth.

It should be noted that the description of the plant which follows, is a detailed one that enables the identification of the plant without regard to certain specific botanical statements, since the plant is clearly identifiable by reason of the certain peculiar differences which reside therein as distinguished from prior existing Dieffenbachia.

I have chosen to designate the instant cultivar by the name 61101 and thus the Pedigree of Dieffenbachia×'61101' may be stated to be the following:

As noted above, the plant of this disclosure was a selection resulting from an extended planned breeding program which is ongoing. The purpose of the breeding program is to expand the range of phenotypic variation within the genus to produce plants having a wider range of adaptation and ornamental value for use as specimen plants which can be container cultured. The plant of this disclosure, '61101' was a selection from the progeny of "39301'×'Memoria Corsii'. The seed parent '39301' was a selection from the cross of "18305'×'12703'. The seed grandparent "18305' was a result of a cross of the named plants 'Wilson's Delight'× 'Camille'. The pollen grandparent '12703' resulted from the cross of '77601' with a species unidentified Dieffenbachia specimen labeled 'CC78'. The parentage of '77601' was a specimen of *D. Hoffmanii* crossed with the named variety 'Camille'. This plant was selected based on its unusual and distinctive expressions of foliar coloration and character, and was seen as immediately unusual in having leaf colors which are actually and discernibly darker on the undersides of the leaves than on the top sides, which are realized to be highly unusual within the species.

As before suggested, the development or discovery of this cultivar in Apopka, Fla., from the progeny of the stated cross was determined by me as being of value from a commercial standpoint.

I have caused asexual propagation of the cultivar by cuttings to increase the number of plants for evaluation and demonstrated the stability of the combination of characteristics from generation to generation.

Asexual propagules of the plant '61101' were grown and observed for novelty and stability under greenhouse conditions which closely approximate those generally used for commercial production at our facilities near Apopka, Fla. Measurements and values of the characteristic expressions from these specimens were recorded from which the plant can be botanically described and botanically distinguished.

While the colors may vary somewhat depending on exposure during culture such as light level and fertilization rate, it does not however provide any variance in genotype.

The traits which I deem important have been repeatedly observed, are determined to be basic characteristics of 61101, and help to distinguish them from other Dieffenbachia currently available and are not like any of those described by the following references:

Bailey, L. H. and E. Z. Bailey, 1976, Hortus Third, MacMillian, New York.

Graf, A. B., 1978, Tropica—Color Cyclopedia of Exotic Plants and Trees, Roehrs Co., East Rutherford, N.J.

The charactertistics may be summarized as including the following unique combinations.

The top surfaces of the leaves are predominately silvery-grey, and are highlighted by white midrib, and a pattern of blotches which is generally less dense with progressive distance from the midrib. Blothes close to the midrib are white, and those most distant to the midrib may be partially or wholly light green. The margins of the lamina are of a darker shade of green than the light green spots, but an even darker green may occur as small spots near the margin and the darkest green may constitute a non-uniform and interrupted marginal variegation.

The bottom surfaces of the leaves are conspicuously darker than the top surfaces and have a midrib which is an intermediate green at the basal portion, and becomes progressively whiter toward the apex of the leaf. Blotches on the bottom surface appear to be of intermixed white and green color, and seem to be most concentrated near the midrib. The margin of these surfaces is more a uniform dark green without the silvery-grey tone of the top surfaces.

The veins of the top surfaces' green portions are of a clearly deeper green than those of the bottom surfaces which are of the same tone as the green shades of the lamina. The spots of the leaves are characteristically irregular in size, shape and location.

As will be observed from a consideration of the drawings appended hereto,

FIG. 1 is a photographic reproduction in full color of a nine-month old plant illustrating the general growth habit and foliar variegation.

FIG. 2 is a photographic print of leaves showing both the top and bottom views to illustrate the unique nature of the foliar variegation. The leaf on the left of FIG. 2, is oriented to show the top surface, while that on the right of the photograph depicts the typical colors and patterns of the bottom leaf surfaces.

DETAILED DESCRIPTION

It should be understood and is I am sure, that the photographic reproductions are as nearly representative of the actual plants as is possible to make the same by this type of illustration and in my judgment are representative of such disclosures and accurate as the eye can determine.

In order to further describe the new Dieffenbachia plant, based on observations made in the greenhouse near Apopka, Fla., where the plant was propagated, I believe the following color references as measured against The Royal Horticultural Society Colour Chart are as nearly accurate as is possible to make the same and colors are approximate as color depends on horticultural practices such as light level, fertilization rate, and leaf age among others.

Overall size and growth habit: In a 15 cm standard pot after approximately 6 months of growth under appropriate conditions from a liner obtained from tissue culture, 61101 will be approximately 65 cm from the soil surface to the tips of the uppermost leaves when held upright. At this stage of growth leaves average approximately 36 cm in length and 16 cm in width. Plants of this size average approximately 3.5 basal shoots. All subsequent measurements are based on the above parameters. The ultimate size of 61101, if planted in a sufficiently large container and grown under appropriate conditions, has not been determined.

Stems: The stem color is not generally visible due to the clasping nature of the petiole wings. Removal of the petiole exposes an area that is made up of two colored areas that are irregular in shape and consists of a lighter area that is RHS 147-D and a darker area that is RHS 144-A. The axillary bud that is also exposed upon removal of the petiole is RHS 147-B. A small area of the stem is visible without removal of the petiole and is RHS 147-A.

Petioles: The petiole consists of two colored areas that blend near the center. The outside edge of the petiole is RHS 146-B while the center of the petiole is RHS 146-D.

Leaves: The leaf midrib is thick and tapers toward the apex. It protrudes prominently from the abaxial side of the leaf and is RHS 155-C. The general background color in the central half of the leaf blade is RHS 191-B while the outer portion of the leaf is 191-A. This area darkens to RHS 189-C in older leaves. The primary leaf veins are sunken into the adaxial side and stand out from the abaxial side of the leaf blade. The color of the primary veins is the same as that of the adjacent leaf blade.

In summary it may be stated that the variegation is disclosed as comprising many small irregular islands RHS 155-B/C scattered throughout the leaf blade. The color of the islands extends through the leaf and is visible when viewed from the other side. There are also some darker islands scattered throughout the leaves that are RHS 191-C. The top surfaces of the leaves are predominately silvery-grey, and are highlighted by a white midrib. A pattern of blotches which is generally less dense with progressive distance from the midrib is expressed. Blotches close to the midrib are white RHS 155-C, and those most distant to the midrib may be partially or wholly light green, near RHS 191-C. The margins of the lamina are of a darker shade of green, RHS 191-B, than the light green spots, but an even darker green near RHS 147-A, may occur as small spots near the margin and this darkest green may constitute a non-uniform and interrupted marginal variegation, and the vein portions which lie over the predominate green of the top surfaces. These are usually less prominent than the white islands.

The backsides of the leaves are generally RHS 147-A and the midribs are RHS 157 B/C. The white islands are also visible on this side and are again RHS 155-C. There are also present some irregularly shaped light green islands that are RHS 144-A.

Axillary shoots: Mature plants may produce up to 4 basal shoots per plant.

Inflorescences: Flowers were not present on plants of the age examined, and are of no ornamental value in Dieffenbachia.

Roots: Thick white roots (RHS 158-C,D) with fine laterals.

I belive the foregoing description will enable a person in the art to identify my particular plant as being distinctive from the others and without necessity to use additional botanical terms, except where they obviously are appropriate.

GENERAL OBSERVATIONS

The plant '61101' grows into a specimen having a single main stem having plural closely adjacent secondary stems, which are basal in source, forming a dense, short mass of high coloration in attractive green tones. The canopy of this plant is unusually attractive in having color splashes which appear to be applied rather than naturally formed; giving a first impression of a synthetic rather than live plant. This genotype offers distinct and unusual characteristics in patterns of coordinated colors, uniformity of leaf sizes and closeness in leaf spacing which give the plant a highly desirable balance and richness of form in most growth stages, and constitutes a resource for these traits. In so doing, '61101' greatly expands the range of expression in available Dieffenbachia plants.

I claim:

1. A new and distinct Dieffenbachia plant, substantially as herein shown and described, characterized particularly as to novelty by the attractive silvery-grey foliage, highlighted by distinct small irregular white patches scattered across the leaf surface, a bright white leaf midrib that sets off the variegated areas within the leaf blade, and a dark green leaf margin that encases the entire variegated area.

* * * * *

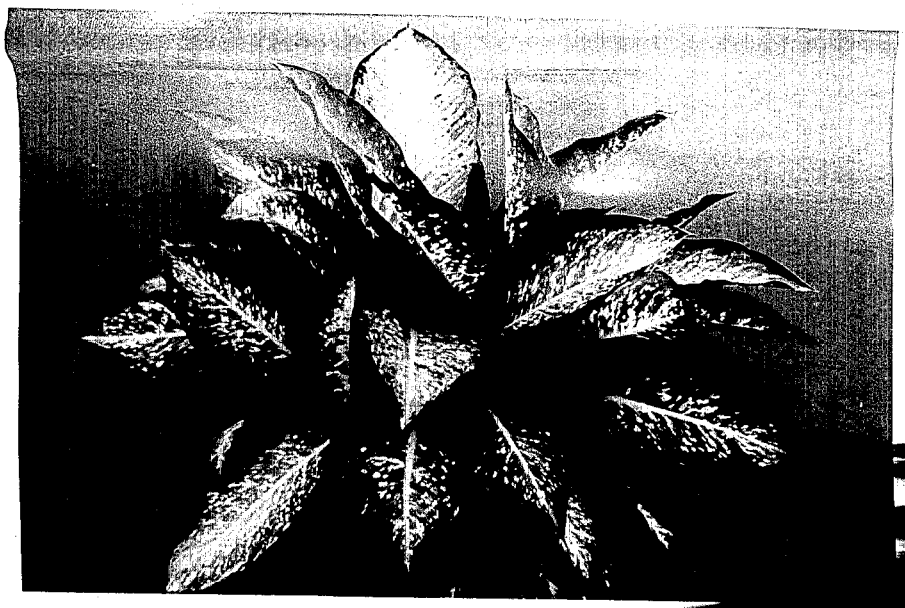
Fig. [illegible]
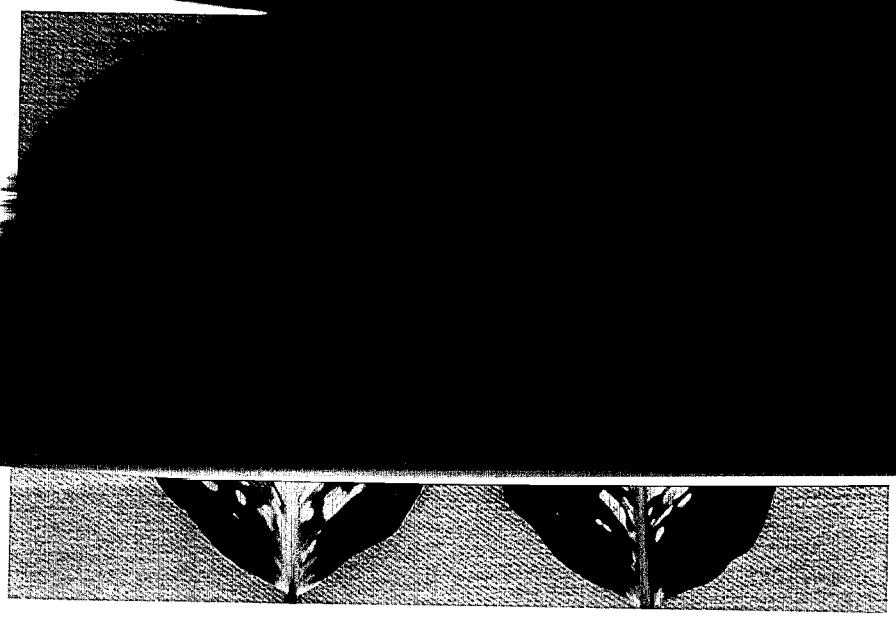
Fig. 2